US006604847B2

(12) United States Patent
Lehrer

(10) Patent No.: US 6,604,847 B2
(45) **Date of Patent: *Aug. 12, 2003**

(54) PORTABLE READING LIGHT DEVICE

(76) Inventor: Robert A. Lehrer, 19528 Ventura Blvd., PMB #316, Tarzana, CA (US) 91356-2917

( * ) Notice: Subject to any disclaimer, the term of this patent is extended or adjusted under 35 U.S.C. 154(b) by 0 days.

This patent is subject to a terminal disclaimer.

(21) Appl. No.: 09/751,148

(22) Filed: Dec. 28, 2000

(65) Prior Publication Data

US 2002/0085372 A1 Jul. 4, 2002

(51) Int. Cl.$^{7}$ .................................................. A61B 1/06

(52) U.S. Cl. ....................... 362/572; 362/105; 362/804; 315/200; 606/8

(58) Field of Search ................................ 362/105, 800, 362/804, 103, 188, 190, 191, 574, 581, 572

(56) References Cited

U.S. PATENT DOCUMENTS 5,086,378 A 2/1992 Prince
5,143,442 A 9/1992 Ishikawa et al.
5,313,188 A * 5/1994 Choi et al. .............. 315/200 A
5,339,223 A * 8/1994 Kremenchugsky et al. . 362/276
5,558,428 A 9/1996 Lehrer et al.
5,630,661 A 5/1997 Fox
5,634,711 A * 6/1997 Kennedy et al. ............ 315/224
5,722,762 A 3/1998 Soll
5,887,965 A * 3/1999 Edens et al. ................ 362/276
5,997,165 A 12/1999 Lehrer
6,021,344 A * 2/2000 Lui et al. .................... 600/476
6,069,689 A * 5/2000 Zeng et al. .................... 356/73
6,200,134 B1 * 3/2001 Kovac et al. ............... 362/800
6,252,254 B1 * 6/2001 Soules et al. ............... 257/100
6,255,670 B1 * 7/2001 Srivastava et al. .......... 257/100
6,290,368 B1 * 9/2001 Lehrer ........................ 362/103
6,294,800 B1 * 9/2001 Duggal et al. ................ 257/89
6,305,818 B1 * 10/2001 Lebens et al. .............. 362/184
6,337,536 B1 * 1/2002 Matsubara et al. ......... 257/461
6,345,903 B1 * 2/2002 Koike et al. ................ 313/512

OTHER PUBLICATIONS

Copy of Brochure.

* cited by examiner

*Primary Examiner*—Sandra O'Shea
*Assistant Examiner*—John Anthony Ward
(74) *Attorney, Agent, or Firm*—Greenberg Traurig

(57) ABSTRACT

A portable reading light device utilizing an LEDs as the source of light mounted in a housing having a single lens through which light from the LEDs is projected, the power to the LEDs being controlled by Pulse Width Modulation.

14 Claims, 5 Drawing Sheets

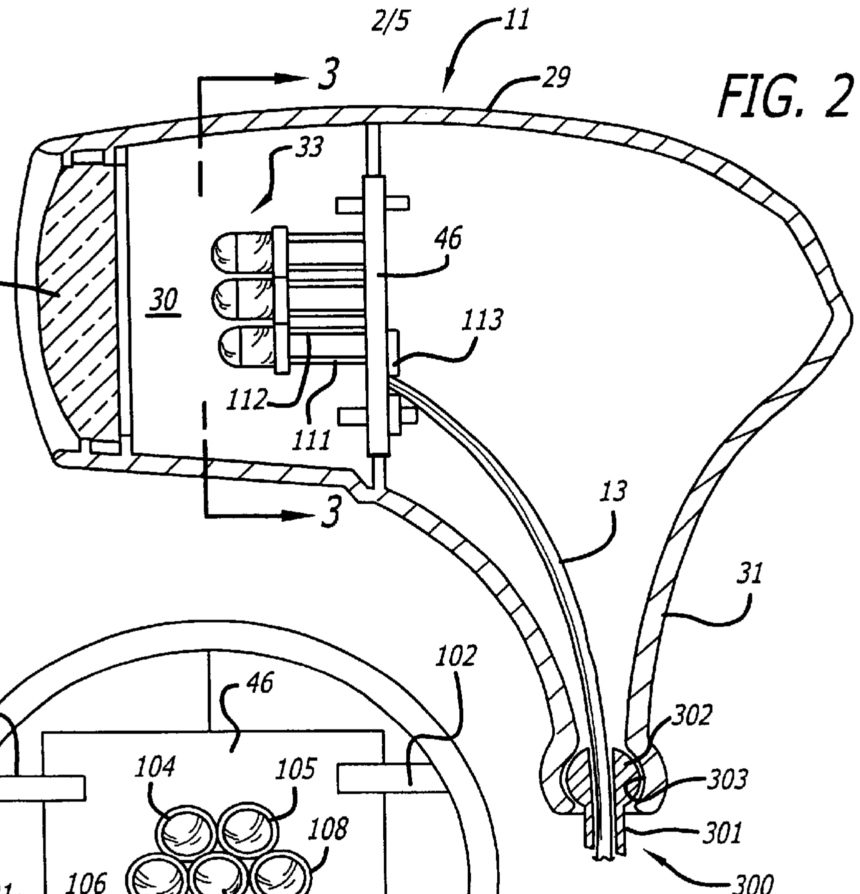
FIG. 2
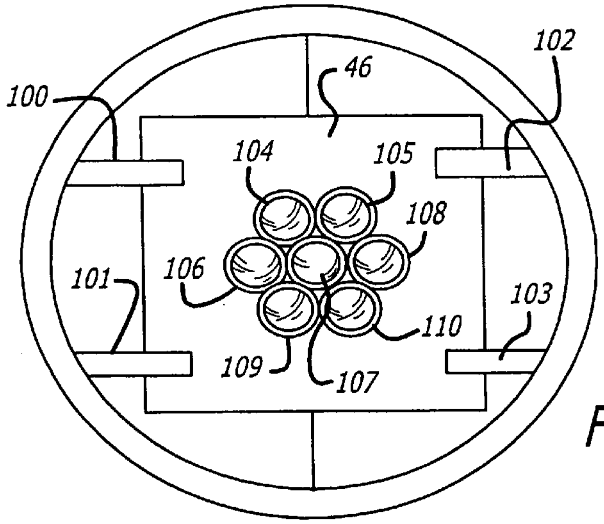
FIG. 3
FIG. 8
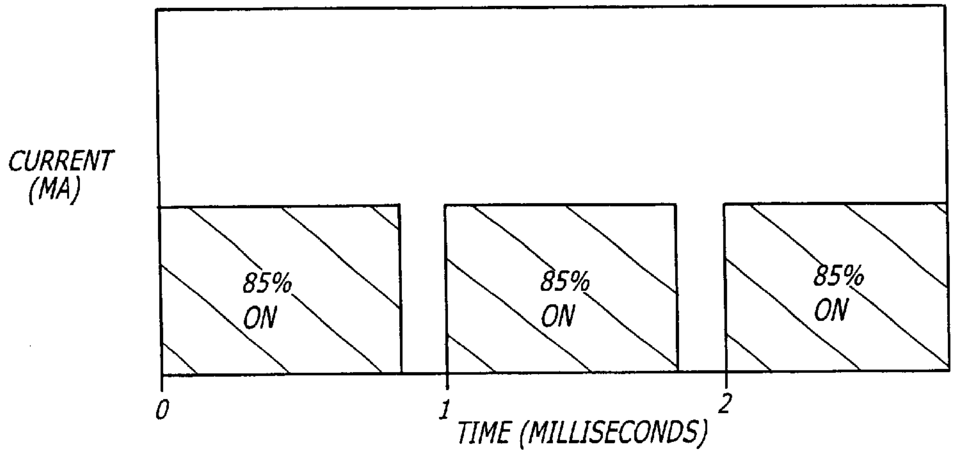

FIG. 4
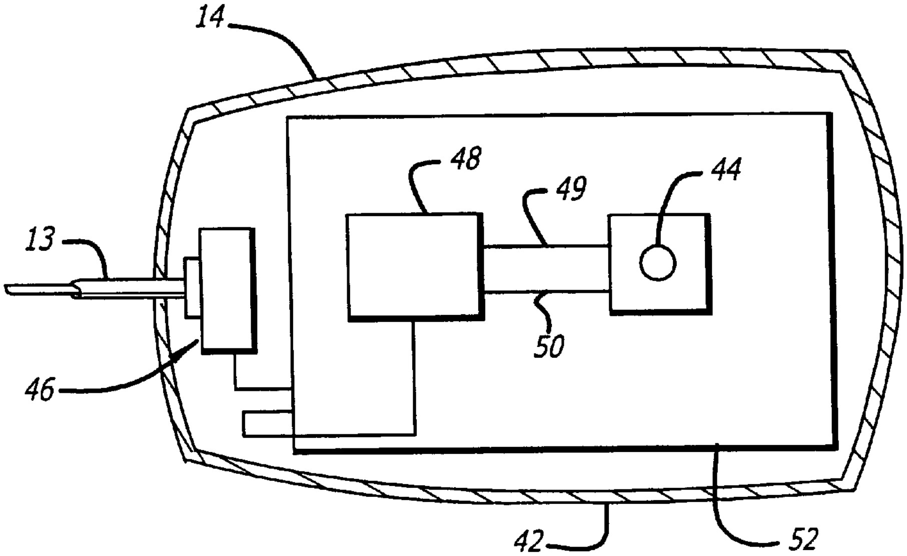
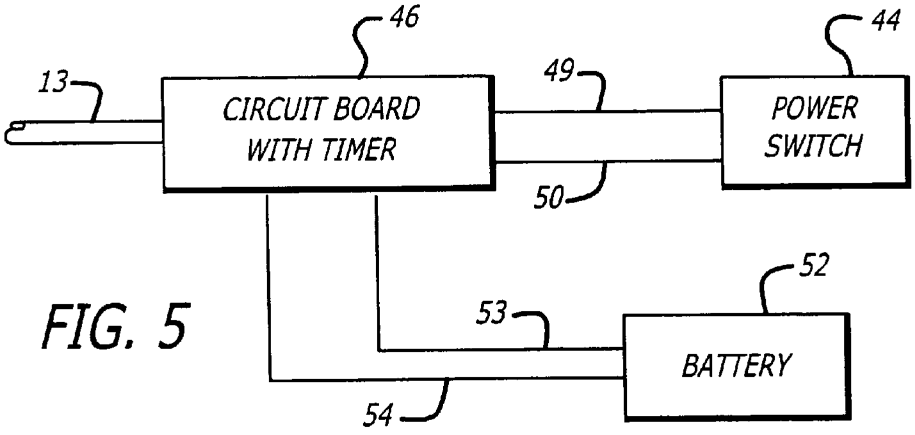
FIG. 5
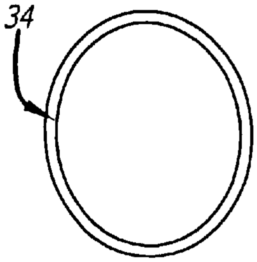
FIG. 6
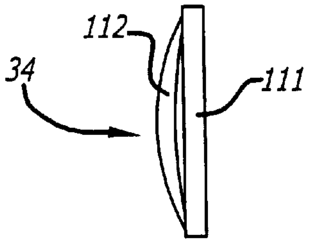
FIG. 7

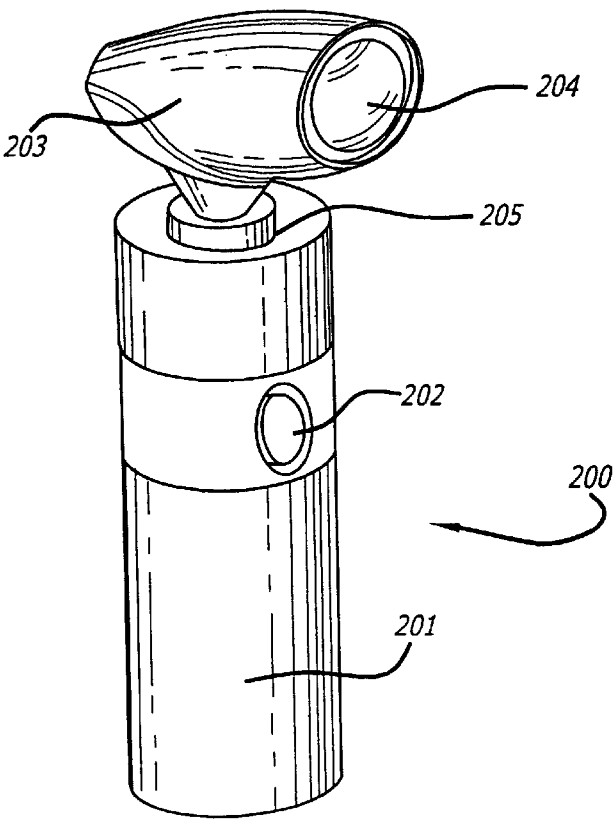
FIG. 9
FIG. 10
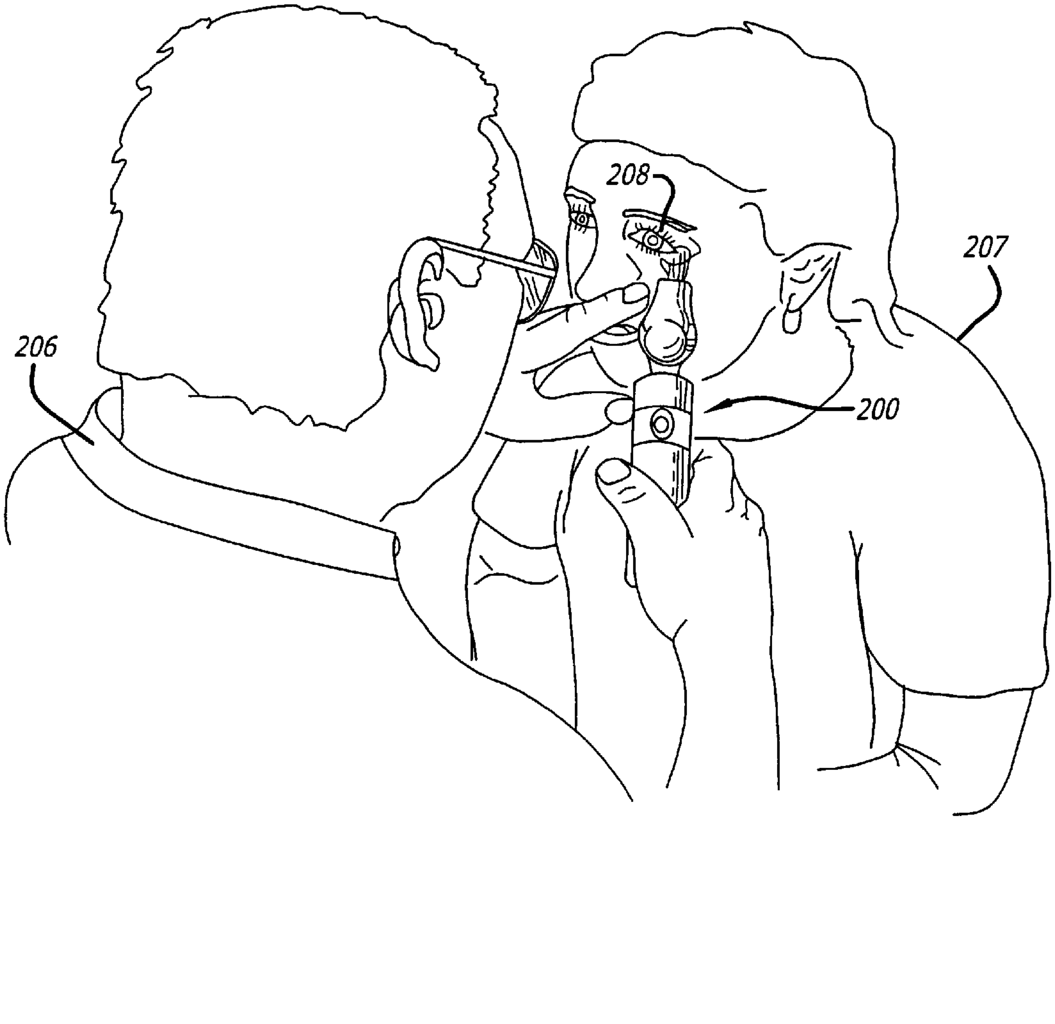

PORTABLE READING LIGHT DEVICE

BACKGROUND OF THE INVENTION

1. Field of the Invention

The invention relates to portable reading lights; and, more particularly, to a light device.

2. Related Art

Reading lights are well known in the art. In my U.S. Pat. No. 5,558,428, I disclose a portable reading light adapted to be worn about the head of a user. The light of the device projects a beam for reading a book or magazine or the like and is adjustable. The light of the device diffuses a beam substantially uniformly over a quadrilateral area so that the user can read a book or magazine with comfort.

Although this light device works quite well, the bulb used, disposed at the head of the user, generates quite a bit of heat. Increasing the intensity of the bulb to increase the amount of light generated would only add to the heat problem.

In my U.S. Pat. No. 5,997,165, I disclose another portable reading light device adapted to be worn about the head of a user or the like. This device utilizes a projection housing adapted to be used as the light source having the terminal end of a fiberoptic mounted therein, the other end extending to a remote lamp unit having a reflector and a light bulb mounted therein.

While this light device also works quite well, fiberoptics are quite expensive and the equipment used to generate the light output is cumbersome and expensive.

In my pending application Ser. No. 09/316,715, filed May 21, 1999, I disclose another type of reading light that generates a bright, focused rectangular light using little power. This reading light uses LEDs as the light source. However, it has been found that, even though this reading light works quite well and projects sufficient light to illuminate a book or the like, most readers, even if they are not aware of it, move their heads (on which the light may be mounted) slightly while reading which causes slight light fall off.

SUMMARY OF THE INVENTION

It is an object of this invention to provide a reading light using LEDs as the output of the light source.

It is still further an object of this invention to carry out the foregoing object directing the light source into a beam thereby making efficient use of light.

It is still further an object of this invention to carry out the foregoing objects spreading the light evenly with uniform illumination than prior art devices.

It is another object of this invention to provide a white light having particular value in certain diagnostic procedures.

These and other objects are preferably accomplished by providing a portable reading light device that utilizes LEDs as the light source focused through a single lens. Pulse Width Modulation is used to actuate the LEDs to provide uniform illumination with less heat than a continuously operating LED.

BRIEF DESCRIPTION OF THE DRAWING

FIG. 2 is a view, partly in section, of the light unit alone of the device of FIG. 1;

FIG. 3 is a view taken along lines 3—3 of FIG. 2;

FIG. 4 is a plan schematic view of the power unit of FIG. 1 with the cover removed;

FIG. 5 is a schematic view of the circuitry of the unit of FIG. 4;

FIG. 6 is an elevational front view of the lens alone of the unit of FIG. 1;

FIG. 7 is a side view of the lens alone of FIG. 6;

FIG. 8 is a graphical illustration of Pulse Width Modulation used to supply power to the LEDs of the unit of FIG. 1;

FIG. 9 is a perspective view of still another embodiment of the invention showing a diagnostic tool using the lighting means of the invention;

FIG. 10 is a perspective view illustrating the use of the tool of FIG. 9;

DESCRIPTION OF THE PREFERRED EMBODIMENT

Figure 1:
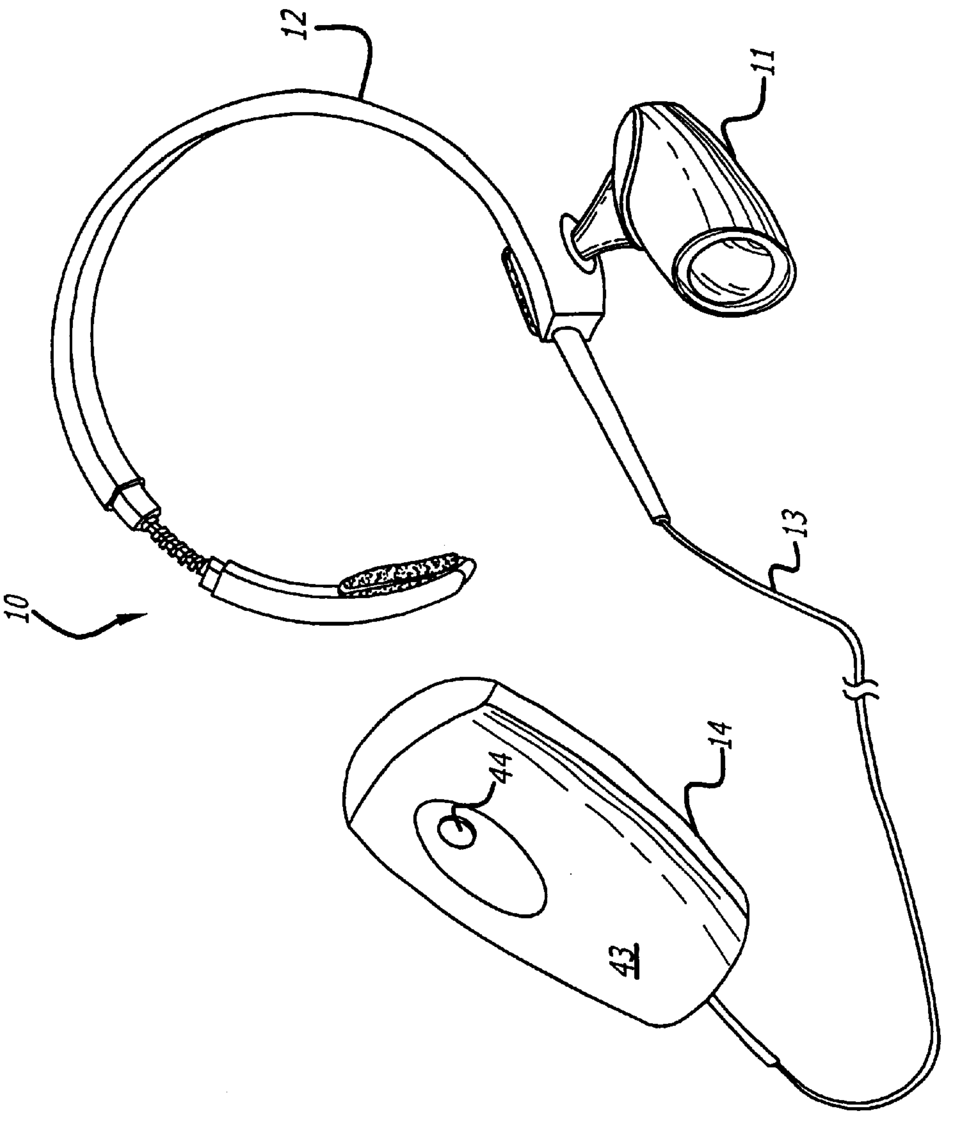
FIG. 1 is a perspective view of a light device that may be worn by a user in accordance with the teaching of the invention.

Referring now to FIG. 1 of the drawing, device 10 is shown comprising a light projection unit 11, a head band 12, a wire conduit 13 and a power unit 14 remote from projection unit 11.

As seen in FIG. 2, light projection unit 11 is mounted to head band 12 in any suitable manner. Preferably, a simple ball swivel arrangement 300 may be used to attach unit 11 to head band 12. Thus, swivel arrangement 300 may have a shaft 301 secured to head band 12 terminating in a ball 302 rotatably mounted in a socket 303 fixed to clamping unit 12. The ball 302 may be rotatable in socket 303 on housing 29 of unit 11. Conduit 13 passes through ball 302 and shaft 301. The ball 302 thus rotates within socket 303 yet retains a fixed position therein until moved due to its frictional relationship therein. The unit 11 thus can be adjusted to project light onto a book as discussed in my prior patents and pending application.

Projection unit 11 is shown in FIG. 2 having a main housing 29, which may be rounded at the rear for aesthetic purposes, and an inner light chamber 30.

Housing 29 may be a one-piece unit of any suitable material, as ABS plastic. Housing 29 has a restricted neck portion 31 at the rear and a plurality of light emitting diodes (LEDs) 33 are mounted in the interior 32 of light chamber 30.

As seen in FIG. 3, although a single LED may be used, preferably a plurality, such as 7 disposed in 2 rows of 2 separated by one row of 3, are provided. These LEDs are in abutting relationship and, as seen in FIG. 3, the lenses have their light beams focused along generally the central axis of the light chamber 30 of housing 29.

Any suitable means may be used to connect light unit 11 to band 12, or to the temple of a pair of glasses or the like, as disclosed in my prior patents and pending application Ser. No. 09/316,715, the teachings of which are incorporated herein by reference.

A lens 34 is mounted at the open end 36 of housing 29.

Although the unit of FIG. 2 may be self-contained, as by having a suitable circuitry coupled to LEDs 33 and a source of electricity, it is preferable that the LEDs 33 be electronically coupled via conduit 13 to power unit 14 (FIG. 1). As seen in FIG. 4, power unit 14 has a main generally elongated rounded housing 42, normally closed off by a cover 43 (FIG. 1), having an on-off switch 44 accessible from the outside.

Housing 29 also includes an LED circuit board 46 (FIG. 5) electronically coupled to the conduit 13 extending from housing 29.

Any suitable electronics may be used to power LEDs 33. For example, power switch 44 may be electronically coupled to a circuit board 46 by leads 49, 50 (see also FIG. 5). Circuit board 46 in turn receives power from battery 52 via lead 53. Lead 54 extends to circuit board 46. Board 46 preferably includes a starter timer circuit as will be discussed.

Again, any suitable electronics, as will be discussed further, may be used. If desired, the timing circuit portion of board 46 may be eliminated. Board 46 may be any suitable state of the art circuit board coupled to a battery that delivers an electronic current to LEDs 33 via conduit 13.

Any suitable source of power may be used, such as alkaline or ni-cad batteries, AC current, etc. Preferably, 4 AA batteries may be used to provide power to circuit board 46 and thus power LEDs 33 with a plug-in transformer to recharge the batteries when plugged in as is well known in the bed lamp art.

As seen in FIG. 3, circuit board 46 is supported within housing 29 by support members 100 through 103 and LEDs 33 are disposed in an array of 7 LEDs, 104 through 110, a first pair of LEDs, LEDs 104 and 105, are separated by 3 aligned LEDs 106, 107 and 108, from a second pair of LEDs 109, 110. Each LED 33, as seen in FIG. 2, is electronically coupled, via a pair of wires 111, 112, to circuit board 46.

Unit 11 may be any suitable dimensions. For example, lens 34 may be about 5.03 mm. thick and spaced, at its point closest to LEDs 33, about 13.18 mm. from the center light source of each LED 33.

Lens 34 is an imaging lens, generally oval in configuration as seen in FIG. 6. It may be about 20.83 mm. wide at its shorter width in FIG. 6 and about 102 mm. wide at its longer width in FIG. 6. As seen in FIG. 7, lens 34 may have a first rear portion 111 facing LEDs 33, generally uniform in thickness, with an integral front spherical or convex portion 112. Portion 111 may be about 2.01 mm. in thickness and lens 34 may be about 5.02 mm. in overall thickness at its thickest point. Portion 112 may have a spherical radius of about 32.99 mm.

Lens 34 may be of any suitable materials, such as an acrylic material. The surfaces may be polished and optically clear. Of course, the foregoing dimensions may vary.

As seen in FIG. 2, each pair of wires 111, 112 is coupled to a resistor 113 on circuit board 46.

As seen in FIG. 3, the LEDs 33 are placed as close together as possible for optimal light beam uniformity and intensity but far enough apart to allow for manufacturing tolerance. With the set up described, unit 11 being about 20" from the page of a book, an oval beam of light, with soft edges of about 12"×14" will result.

The circuitry of FIGS. 4 and 5 can be used to apply more current to LEDs 33. This increase in current results in more light output from the LEDs 33. Thus, Pulse Width Modulation (PWM) may be used to turn each LED on for a period of time, and then turn each LED off for a short period of time. This allows one to increase the current supplied to the LED. PWM allows the LED to cool off slightly every time the LED is turned off, avoiding the thermal degradation which leads to increased failure rates and a loss of life. Control of the LED is done using a microprocessor to determine the amount of time the LED is on and off. The amount of "on" time vs. the amount of "off" time is a function of the current being supplied to the LED. A higher current results in more "off" time, which allows the LED to cool.

If you apply more current to the LED without using PWM, the LED would likely overheat, causing a higher failure rate and a decrease of expected life. Using a lower current and a longer "on" time results in a white light. A side benefit is the resistors used in combination with the LEDs 33 run cooler.

FIG. 8 illustrates how PWM increases the light output of LEDs 33. The PWM has a duty cycle of 85% and flashes approximately 1000 times per second. These values may vary slightly depending on temperature and battery power.

The image projected by unit 11 is oval, substantially close to a 13" circle, due to the placement and number of LEDs and the lens 34. The back of lens 34, facing LEDs 33, is planar. The image projected eliminates hot spots; that is, it is substantially evenly bright across the entire projected image due to the distance from the LEDs to the lens 34 and the curvature of the lens. The rays of light coming from the lens are captured by the lens and collimated into a uniformly lit image.

PWM is used to turn on and off the LEDs, about 1,000 times per second. This increases current to the LEDs but the LEDs are not on 100% of the time. They are on about 85% of the time. This is called the duty cycle. This results in the LEDs, which are blue, giving off a white light.

Although a headpiece 12 is disclosed, my prior patents and pending application, the teachings of which are incorporated herein by reference, show other ways in which unit 11 may be mounted to the head of a user. Movement of the user's head during reading does not affect the overall illumination of the page of the book or the like on which beam of light projected.

Power switch 44 is used to turn the unit on and off.

It can be seen that the combination of the placement and number of LEDs 33, a single lens and a portable power source, along with PWM, results in a high beam output with no humanly detectable heat at the output of the light housing.

The starter portion simply resets and initializes the timer portion in the starting and timing circuit. The starting and timing circuit is the heart of this subsystem. The timing circuit portion may use a simple linear integrated timer in a one shot configuration to control a switching relay. When power has been applied to the timing circuit portion, the starter portion can then be used to reset and initialize the timer portion. Upon initialization, the timer portion closes the switching relay which turns on the LEDs 33 and starts counting for its preset time period. When the preset time period has expired, the time portion opens the switching relay which turns off the LEDs 33. The timing circuit will shut off the light after a predetermined period of time of use to save batteries or the like if the user fell asleep or otherwise did not turn it off.

Any suitable LEDs may be used. For example, white light emitting milky diffusion-type LEDs are preferred. A single LED having a typical luminosity of about 0.48 cd is preferred. An LED that emits light with 70° angle of directivity may be used. LEDs having a weight of less than about 0.5 grams may be used. Phosphor coated LEDs may be used which emit a white light. Although one or more of such LEDs may be used, I prefer to use 7 disposed as previously discussed. As used throughout, "white," in reference to an LED, does not refer to the actual color of the LED but the light emitted.

Any suitable dimensions may be used. For example, the housing 29 may be 46 mm. long and about 26 mm. in diameter.

In order to minimize projected ghosts, e.g., stray light rays, the inside of the unit housing 19 may be flat black or made of a non-reflective material so that there are no internal reflections. However, if desired, the housing 19 may be of a translucent material. In order to increase reliability, switching transistor may be used in place.

Although disclosed primarily as a reading light or lamp, my invention can be used by doctors, optometrists, dentists, etc. or anywhere a bright focused white light or any suitable colored light, such as red, is desired.

The brightest of the LEDs may be controlled by turning the same on and off rapidly which lowers the flash rate and does not affect the steadiness of the light beam to the reader. This may be accomplished by pulse width modulation as is well known in the art. Thus, a conventional microprocessor may be used having software therein for automatically shutting off the timer of the timing circuit after a predetermined period of time, for dimming the light output and providing the Pulse Width Modulation for turning the LEDs on and off at a high rate of speed to control their brightness.

As seen in FIG. 9, a diagnostic tool 200 is shown having an elongated handle 201, an on-off button 202, and a light housing 203 and lens 204. Light housing 203 may be swivelly attached, at connection 205, to handle 201, similar to aforementioned ball and socket arrangement 300. Lens 204 may be similar to aforementioned lens 34 and it is to be understood that the inner electronics of tool 200 is identical to the electronics of the embodiment of FIGS. 1–5, as seen in the interior of housing 14 in FIG. 4.

Thus, as seen in FIG. 10, a medical practitioner 206 shines the light from tool 200 in the eye 208 of a patient 207 to examine the same.

The following steps are then carried out to activate the LEDs:

Pulse width modulation is used to apply a current of about 20 milliamps to the LED means for a total period of about 1 millisecond while flashing the current evenly on and off during that period about 1000 times per total period so that the current is supplied to said LED means for about 0.85 milliseconds of the 1 millisecond total period and the current is ceased to the LED means about 0.15 milliseconds of the 1 millisecond total period.

Thus, the white light produced has particular application in certain medical diagnostics. In this regard, although any suitable LEDs will produce a light sufficient for use as a reading lamp, I have found unexpectedly that the selection of certain LEDs, their placement as discussed above, and the use of PWM will produce an extremely white light having particular application for certain medical diagnostics. Such white light has surprisingly and unobvious superiority over conventional light sources which contain significant yellow and other color spectral impurities. With white light, better and more sensitive diagnoses can be made. For example, jaundice is a disease that manifests itself by yellowish pigmentation of one's skin, tissues, and body fluids caused by the deposition of bile pigments. Traditional lighting sources with their yellow or other color components may mask the disease or its severity.

Because this light is much whiter than traditional light sources, it gives the unexpected result of earlier detection of disease where the color of one's skin, eyes, or body fluids is critical than was previously possible. White light causes a more accurate and sensitive diagnosis than traditional light sources.

This extremely white light is produced by the selection of specific LEDs, such as high power white LEDs having a spectral radiance that peaks at less than 500 nanometers.

Figure 11:
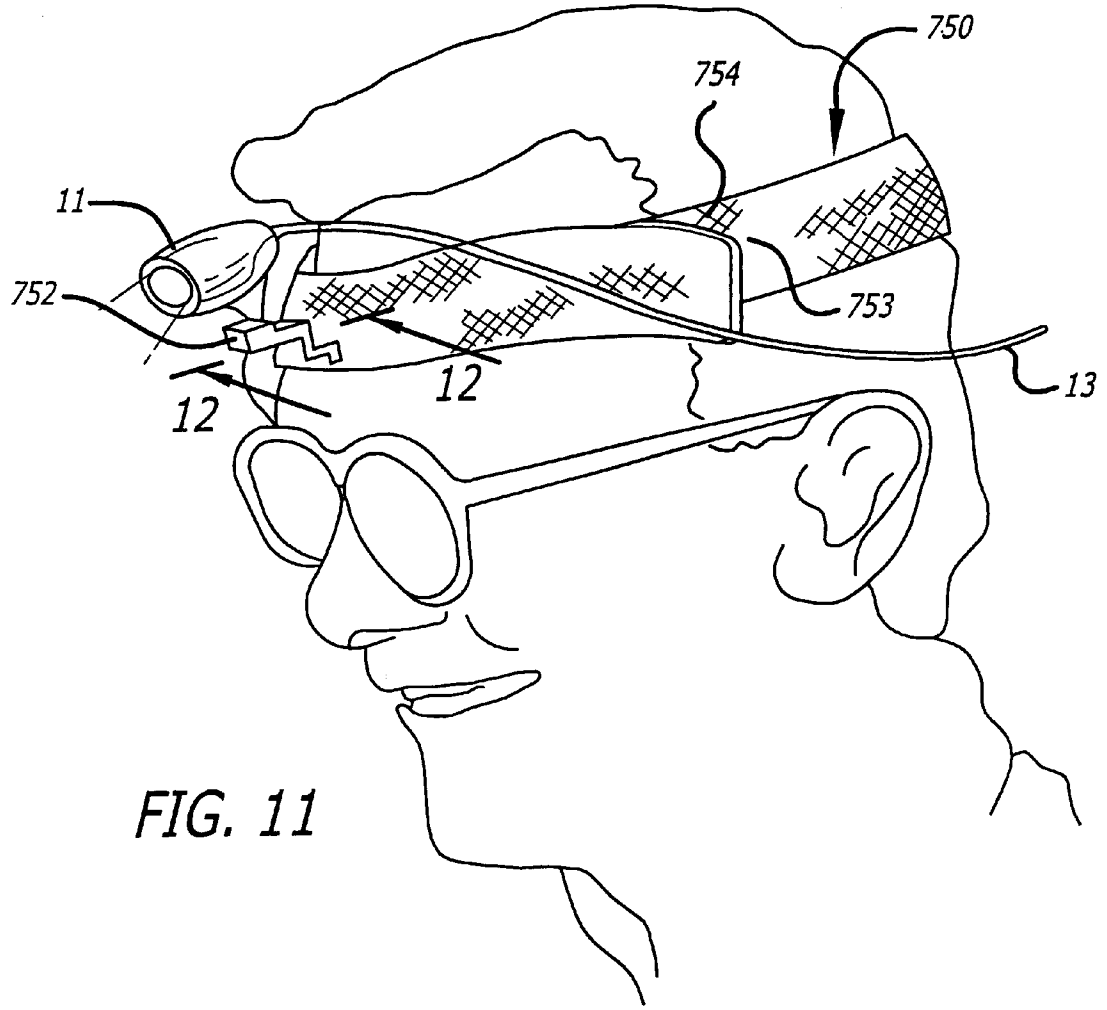
FIG. 11 is a perspective view of a further embodiment of the invention.
Figure 12:
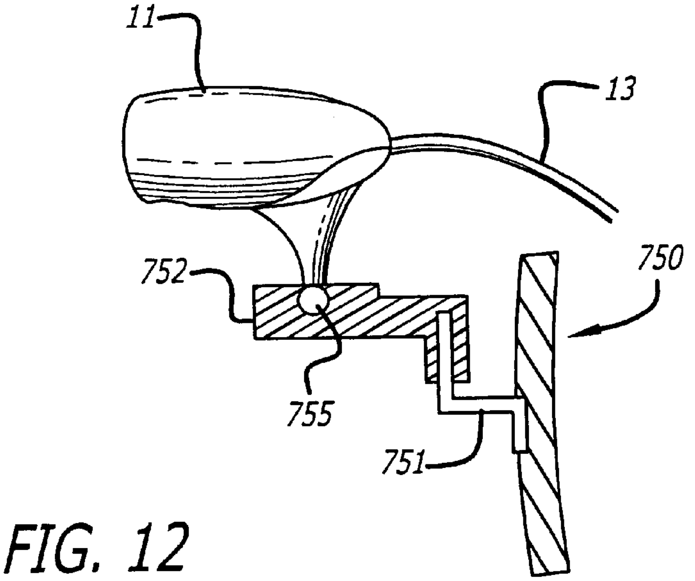
FIG. 12 is a view taken along line 12 of FIG. 11.

Essentially the same light can be worn using a headband by a surgeon or doctor. This is shown in FIG. 11 wherein unit 11 of FIG. 2 is mounted to the adjustable head band 750 of a user. This may be accomplished in any suitable manner, such as by having an L-shaped flange 751 (FIG. 12) fixed to head band 750 to which clamping unit 752 and unit 11 may be secured to. Thus, the position of unit 11 and clamp 752 may be adjustable to vary the direction of the light output. Headband 750 may be adjustable using mating pieces of Velcro® material 753, 754 in the manner discussed in my U.S. Pat. No. 5,558,428. Conduit 13 is identical to conduit 13 in FIG. 1 leading to power supply 14. Unit 11 of FIGS. 1, 11 and 12 are identical excerpt that a ball and socket joint 755 may be used to swivelly mount unit 11 to clamping unit 752. Thus, a doctor or surgeon is provided with an extremely white light for diagnostic purposes.

The LEDs used herein, their number and placement, which can be varied, along with Pulse Width Modulation (PWM) provides a bright white light that runs cooler and at a lower temperature than conventional lights. The use of PWM provides a desired color temperature which can be above 8500 K whereas incandescent lighting is at 3200 K or lower. Thus, a color temperature above about 7000 K is desirable.

The LEDs selected may be of any suitable type to produce a white light. For example, although referred to as White LEDs, one preferred embodiment that can be used is a yellow phosphor compound contained in a resin, the resin appearing yellow when it absorbs the light from the blue LED. The resultant beam is white. The current supplied to the LEDs may be about 10 to 20 milliamps. The combination of duty cycle and current supplied converts the light of the LEDs to a bright white light.

The unit 11 is extremely light in weight due to the use of LEDs. The white light produced has particular application for diagnostic purposes, particularly where a true white light is required, such as in the diagnosis and treatment of yellow jaundice, or liver disorders. The unit 11 of FIGS. 9 and 11 has particular application in examining patient's eyes. The unit 11 may be head mounted, as in FIG. 11, emitting a beam of white light that is brighter and stronger than an opthalmoscope and can be used in such treatment along with use in surgery. It is extremely light weight and more comfortable than prior head mounted lights.

It can be seen that there is disclosed an improved bed lamp having a high light projection eliminating heat at the output. The light from the LEDs provides a clean bright white light easy on the eyes which may be in a oval pattern. The size of the image falling on the book or the like may be adjustable. Although a particular embodiment of the invention is disclosed, variations thereof may occur to an artisan and the scope of the invention should only be limited by the scope of the appended claims.

I claim:

1. A portable lightweight lamp comprising:

a light projection housing open at one open and terminating in a light output opening at the other end;

LED means mounted in said housing at one end thereof for emitting a source of light; and focusing lens means mounted in said housing remote from said LED means receiving therethrough the light emitted by said LED means and projecting a focused beam of light out of the housing.

2. A portable lightweight lamp comprising:

a light projection housing open at one open and terminating in a light output opening at the other end;

LED means mounted in said housing at one end thereof for emitting a source of light, said LED means having a color temperature above about 7000° K; and focusing lens means mounted in said housing remote from said LED means receiving therethrough the light emitted by said LED means and projecting a focused beam of light out of the housing.

3. The lamp of claim 2 wherein said color temperature is about 8500° K.

4. A portable lightweight lamp comprising:

a light projection housing open at one open and terminating in a light output opening at the other end;

LED means mounted in said housing at one end thereof for emitting a source of light, said LED means having a spectral radiance that peaks at less than 500 nanometers; and focusing lens means mounted in said housing remote from said LED means receiving therethrough the light emitted by said LED means and projecting a focused beam of light out of the housing.

5. A portable lightweight diagnostic tool for a doctor or surgeon comprising:

a light projection housing open at one open and terminating in a light output opening at the other end;

LED means mounted in said housing at one end thereof for emitting a source of white light; and focusing lens means mounted in said housing remote from said LED means receiving therethrough the light emitted by said LED means and projecting a focused beam of light out of the housing, said means including a lens mounted in a position spaced from said LED means whereby said light emitted by said LED means passes through said lens and is projected as a focused beam of light out of the housing.

6. A portable lightweight lamp comprising:

a light projection housing open at one open and terminating in a light output opening at the other end;

LED means mounted in said housing at one end thereof for emitting a source of light;

focusing lens means mounted in said housing remote from said LED means receiving therethrough the light emitted by said LED means and projecting a focused beam of light out of the housing; and pulse width modulation means for applying a current of about 20 milliamps to said LED means for a total period of about 1 millisecond while flashing said current evenly on and off during that period about 1000 times per total period so that said current is supplied to said LED means about 0.85 milliseconds of said 1 millisecond total period and said current is ceased to said LED means about 0.15 milliseconds of said 1 millisecond total period.

7. The method of activating one or more LEDs comprising the steps of:

applying a current of about 20 milliamps to said one or more LEDs for a total period of about 1 millisecond while flashing said current evenly on and off during that period about 1000 times per total period so that said current is supplied to said or more LEDs about 0.85 milliseconds of said 1 millisecond total period and said current is ceased to said one or more LED about 0.15 milliseconds of said 1 millisecond total period.

8. The method of claim 7 wherein said one or more LEDs includes a lens and the step of applying current to said one or more LEDs includes the step of applying current to at least one blue LED with a phosphor resin material applied to the lens of the LED to create a color close to white.

9. A method for providing a white beam of light particularly suitable for diagnostic treatment of jaundice, liver disorders and other diseases where a pure beam of white light is desired including the steps of:

providing a light projection housing opening at one end and terminating in a light output opening at the other end; and mounting LED means having a spectral radiance that peaks at less than 500 nanometers and a color temperature above about 7000° K in said housing at one end thereof emitting said white light.

10. The method of claim 9 wherein the step of mounting said LED means includes the step of mounting LED means having a color temperature of about 8500° K.

11. The method of diagnosing a patient comprising the steps of:

projecting a white beam of light from at least one LED on to the skin, eyes, body tissues or body fluids of a patient in order to detect jaundice and other liver diseases that may be present in the patient in the color of the patient's skin, eyes, body tissues or body fluids while applying current to said at least one LED.

12. The method of claim 11 wherein the step of projecting a white beam includes the step of projecting a light beam from a plurality of LEDs and the step of applying a current includes the step of pulsing said current using Pulse Width Modulation.

13. The method of claim 11 wherein the step of projecting a white beam of light from at least one LED includes the step of projecting a light beam using at least one blue LED coated with a yellow phosphor compound contained in a resin, the resin appearing yellow when it absorbs the light from the blue LED resulting in a white beam of light.

14. The method of claim 11 wherein the step of projecting a white beam of light includes the step of projecting said beam of light at a color temperature above about 7000° K.

* * * * *